US009109023B2

(12) United States Patent
Wang

(10) Patent No.: US 9,109,023 B2
(45) Date of Patent: Aug. 18, 2015

(54) TREATMENT OF INFLAMMATORY DISEASES BY INHIBITING COLD-INDUCIBLE RNA-BINDING PROTEIN (CIRP)

(71) Applicant: The Feinstein Institute for Medical Research, Manhasset, NY (US)

(72) Inventor: Ping Wang, Roslyn, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 14/196,354

(22) Filed: Mar. 4, 2014

(65) Prior Publication Data

US 2014/0186353 A1   Jul. 3, 2014

Related U.S. Application Data

(63) Continuation of application No. 13/264,205, filed as application No. PCT/US2010/030824 on Apr. 13, 2010, now Pat. No. 8,703,138.

(60) Provisional application No. 61/212,584, filed on Apr. 13, 2009.

(51) Int. Cl.
*A61K 39/395* (2006.01)
*A61K 39/00* (2006.01)
*C07K 16/18* (2006.01)

(52) U.S. Cl.
CPC ........... *C07K 16/18* (2013.01); *A61K 2039/505* (2013.01)

(58) Field of Classification Search
None
See application file for complete search history.

(56) References Cited

U.S. PATENT DOCUMENTS

| 5,919,661 A | 7/1999 | Hillman et al. |
| 8,703,138 B2 | 4/2014 | Wang |
| 2014/0193412 A1 | 7/2014 | Wang et al. |

FOREIGN PATENT DOCUMENTS

| CN | 1589279 A | 3/2005 |
| CN | 1980649 A | 6/2007 |
| WO | WO 01/09387 A1 | 2/2001 |
| WO | WO 2009/090287 A1 | 7/2009 |
| WO | WO 2010/120726 A1 | 10/2010 |

OTHER PUBLICATIONS

Qiang et al. 2013. Nature Med. 19:1489-1497.*
Notification of Transmittal of the International SEarch Report and the Written Opinion of the International Searching Authority for PCT/US2014/057141, "Peptides Inhibiting Cold-Inducible RNA Binding Protein Activity", date of mailing Jan. 27, 2015.
Xia, Z., et al., "Cold-Inducible RNA-binding (CIRP) Regulates Target mRNA Stabilization in the Mouse Testis", FEBS Letters, 586:3299-3308 (2012).
Notification of Transmittal of the International Search Report and the Written Opinion of the International Searching Authority, or the Declaration, International Search Report and Written Opinion in International Application No. PCT/US2010/030824, 18 pages, mailed Sep. 20, 2010.
Notification Concerning Transmittal of International Preliminary Report on Patentability and International Preliminary Report on Patentability in International Application No. PCT/US2010/030824, 10 pages, mailed Oct. 27, 2011.
Artero-Castro, A., et al., "Cold-Inducible RNA-Binding Protein Bypasses Replicative Senescence in Primary Cells Through Extracellular Signal-Regulated Kinase 1 and 2 Activation," *Molecular and Cellular Biology*, Apr. 2009 LNKD-PUBMED:19158277, vol. 29, No. 7, Jan. 21, 2009, pp. 1855-1868, XP002594596 ISSN: 1098-5549. DOI: http://dx.doi.org/10.1128/MCB.01386-08.
Fujita, J., "Cold Shock Response in Mammalian Cells," *Journal of Molecular Microbiology and Biotechnology*, Horizon Scientific Press, Wymondham, GB, vol. 1, No. 2, Jan. 1, 1999, pp. 243-255, XP007912820 ISSN: 1464-1801.
van Venrooy, S., et al., "Cold-Inducible RNA Binding Protein (CIRP), a Novel XTcf-3 Specific Target Gene Regulates Neural Development in Xenopus," *BMC Developmental Biology*, 2008 LNKD-PUBMED:18687117, vol. 8:77, 2008, XP002594597 ISSN: 1471-213X. DOI: http://dx.doi.org/10.1186/1471-213X-8-77.
Yang, C., et al., "The UV-Inducible RNA-Binding Protein A18 (A18 hnRNP) Plays a Protective Role in the Genotoxic Stress Response," *the Journal of Biological Chemistry*, Dec. 14, 2001 LNKD-PUBMED:11574538, vol. 276, No. 50, Dec. 14, 2001, pp. 47277-47284, XP002594598 ISSN: 0021-9258. DOI: http://dx.doi.org/10.1074/jbc.M105396200.
Zeng, Y., et al., "Down-Regulating Cold Shock Protein Genes Impairs Cancer Cell Survival and Enhances Chemosensitivity." *Journal of Cellular Biochemistry*, May 1, 2009 LNKD-PUBMED:19277990, vol. 107, No. 1, Mar. 10, 2009, pp. 179-188, XP002594595 ISSN: 1097-4644.
Lleonart, M.E., "A New Generation of Proto-Oncogenes: Cold-Inducible RNA Binding Proteins," *Biochemica et Biophysica Acta*, 1805:43-52 (2010).
De Leeuw, F., et al., "The Cold-Inducible RNA-Binding Protein Migrates from the Nucleus to Cytoplasmic Stress Granules by a Methylation-Dependent Mechanism and Acts as a Translational Repressor," *Experimental Cell Research*, 313:4130-4144 (2007).
Peng, Y., et al., "Cold-Inducible RNA Binding Protein is Required for the Expression of Adhesion Molecules and Embryonic Cell Movement in *Xenopus laevis*," Biochemical and Biophysical Research Communications, 344:416-424 (2006).
Hunt, K. K. and Vorburger, S. A., "Hurdles and Hopes for Cancer Treatment," *Science*, 297:415-416 (2002).
Romano, G., "Gene Transfer in Experimental Medicine," *Drug News Prospect*, 16(5):267-276 (2003).
Leung, R. K. M. and Whittaker, P. A., "RNA Interference: from Gene Silencing to Gene-Specific Therapeutics," *Pharmacology and Therapeutics*, 107:222-239 (2005).
Nishiyama, H., et al., "A Glycine-Rich RNA-Binding Protein Mediating Cold-Inducible Suppression of Mammalian Cell Growth," *The Journal of Cell Biology*, 137(4):899-908 (1997).
Zeng, Y., et al., "Down-Regulating Cold Shock Protein Genes Impairs Cancer Cell Survival and Enhances Chemosensitivity," *Journal of Cellular Biochemistry*, 107:179-188 (2009).

* cited by examiner

*Primary Examiner* — Shulamith H Shafer
(74) *Attorney, Agent, or Firm* — Hamilton, Brook, Smith & Reynolds, P.C.

(57) ABSTRACT

Disclosed are pharmaceutical compositions comprising a CIRP inhibitor. A method of treating a subject suffering from an inflammatory condition comprising administering to said subject a CIRP inhibitor is also described herein.

7 Claims, 8 Drawing Sheets

```
          10         20         30         40         50         60
MASDEGKLFV GGLSFDTNEQ SLEQVFSKYG QISEVVVVKD RETQRSRGFG FVTFENIDDA
          70         80         90        100        110        120
KDAMMAMNGK SVDGRQIRVD QAGKSSDNRS RGYRGGSAGG RGFFRGGRGR GRGFSRGGGD
         130        140        150        160        170
RGYGGNRFES RSGGYGGSRD YYSSRSQSGG YSDRSSGGSY RDSYDSYATH NE
```

FIG. 1

TREATMENT OF INFLAMMATORY DISEASES BY INHIBITING COLD-INDUCIBLE RNA-BINDING PROTEIN (CIRP)

RELATED APPLICATIONS

This application is a continuation of U.S. application Ser. No. 13/264,205, which is the U.S. National Stage Application of International Application No. PCT/US2010/030824 filed on Apr. 13, 2010, published in English, which claims the benefit of U.S. Provisional Application No. 61/212,584, filed on Apr. 13, 2009. The entire teachings of the above applications are incorporated herein by reference.

GOVERNMENT SUPPORT

This invention was made with government support under grant RO1 HL 076179 awarded by the National Institutes of Health. The Government has certain rights in the invention.

INCORPORATION BY REFERENCE OF MATERIAL IN ASCII TEXT FILE

This application incorporates by reference the Sequence Listing contained in the following ASCII text file, filed concurrently herewith:

File name: 32681019010SEQLIST.txt; created Mar. 4, 2014, 4 KB in size.

BACKGROUND OF THE INVENTION

Inflammation is the complex biological response of vascular tissues to harmful stimuli, such as pathogens, damaged cells, or irritants. It is a protective attempt by the organism to remove the injurious stimuli as well as initiate the healing process for the tissue. In the absence of inflammation, wounds and infections would heal at best more slowly and progressive destruction of the tissue would compromise the survival of the organism. However, inflammation which runs unchecked can also lead to a host of diseases.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

Despite recent advances in the management of patients with acute inflammatory conditions (e.g. sepsis, trauma-hemorrhage, and gut ischemia-reperfusion injury), a large number of those patients die of the ensuing circulatory shock and multiple organ failure. Shock and multiple organ failure continue to be the leading cause of death in medical and surgical intensive care units with unacceptably high mortality rates. Even though numerous modalities and substances have been studied to prevent circulatory collapse and to reduce mortality, none have been entirely successful.

Today modern medicine is starting to acknowledge that chronic inflammation is the main contributing factor to chronic degenerative diseases. Pro-inflammatory cytokines are the part of our immune system that can attack and kill cells with oxidative chemicals. If left untreated, inflammation can damage tissues and organs. For example, inflammation causes cartilage degradation in patients with arthritis and damage to the pancreas in patients with diabetes; and is now thought to play a role in the cardiovascular disease and cancers.

So far, only extremely limited specific therapies exist for treatment of both acute and chronic human inflammatory conditions. Accordingly, there is a great unmet medical need for an effective novel therapy for inflammatory conditions with minimal side effects.

SUMMARY OF THE INVENTION

The present invention is based on the discovery that the inhibition of Cold-Inducible RNA-Binding Protein (CIRP) attenuates inflammatory responses. More specifically, Applicant has discovered that inhibition of CIRP decreases levels of aspartate aminotransferase (AST), liver myeloperoxidase (MPO), lactate, TNF, serum TNF and serum, lung and liver IL-6 in animal models of hemorrhagic shock compared with untreated control. (FIGS. 7-8). In addition, inhibition of CIRP decreases hemorrhage-induced mortality (FIG. 6). Based on this discovery, pharmaceutical compositions and methods for treatment of inflammatory conditions are disclosed.

In one embodiment, the present invention is a pharmaceutical composition comprising a pharmaceutically acceptable carrier or diluent and a CIRP inhibitor.

In another embodiment, the present invention is a method of treating a subject with an inflammatory condition, comprising administering to the subject an effective amount of a CIRP inhibitor.

In another embodiment, the present invention is an isolated antibody that specifically binds to CIRP (a "CIRP antibody") or an antigenic fragment thereof, wherein said antibody or antigenic fragment inhibits one or more biological activities of CIRP.

In another embodiment, the present invention is a method of inhibiting CIRP activity, comprising administering to a subject in need thereof an effective amount of a CIRP inhibitor.

BRIEF DESCRIPTION OF THE DRAWINGS

FIG. 1 is the human CIRP amino acid sequence (SEQ ID NO 1).

DETAILED DESCRIPTION OF THE INVENTION

Figure 2:
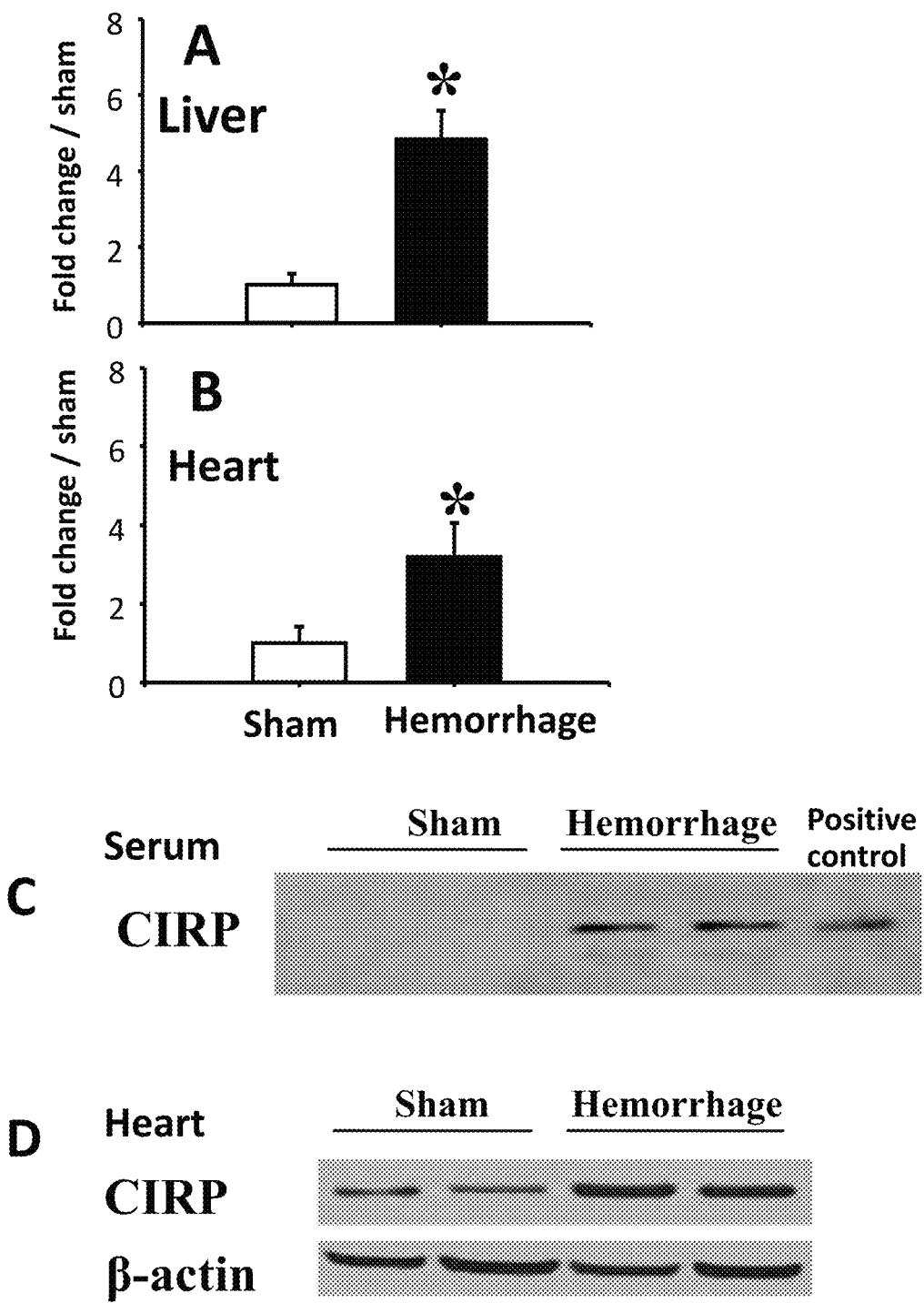
FIG. 2 illustrates the over-expression of CIRP gene in the liver, heart and blood in animal models of hemorrhage compared with sham (not blood) control.

Applicant surprisingly discovered that during an inflammatory response, CIRP expression is upregulated and is released into the circulation. Applicant has also discovered that once CIRP enters the blood stream, it acts as a potent proinflammatory mediator or cytokine and causes tissue injury and even death.

The present invention is based on the discovery that inhibition of CIRP leads to reduction in levels of inflammatory mediators and markers including but not limited to, aspartate aminotransferase (AST), liver myeloperoxidase (MPO), lactate, TNF, serum TNF and serum, lung and liver IL-6 in animal models of sepsis compared with untreated control. These decreases reflect and in some cases account for the beneficial effects of targeting CIRP in the treatment of inflammatory disease and conditions. Moreover, these decreases illustrate the therapeutic benefit of CIRP inhibitors and antagonist in the treatment of such diseases and conditions.

CIRP is a mammalian, preferably human protein induced in cultured cells by mild cold stress (32° C.). CIRP comprises an N-terminal RNA-binding domain and a C-terminal Glycine-rich domain. The amino acid sequence of human CIRP is provided in FIG. 1, SEQ ID NO:1 (see Nishiyama et al. The Journal of Cell Biology, Volume 137, 1997). "Mammalian CIRP" includes proteins having an amino acid sequence which is the same as that of a naturally occurring or endogenous corresponding mammalian CIRP (e.g., recombinant proteins, synthetic proteins (i.e., produced using the methods of synthetic organic chemistry)). The term also includes polymorphic or allelic variants, and other isoforms of a CIRP (e.g., produced by alternative splicing or other cellular processes), and modified or unmodified forms of the foregoing (e.g., lipidated, glycosylated, and unglycosylated. Such proteins can be recovered or isolated from a source which naturally produces mammalian CIRP. CIRP plays an essential role in cold-induced suppression of cell proliferation.

As defined herein, a "CIRP inhibitor" is an agent (e.g., molecule, a natural or synthetic nucleic acid or nucleic acid analog, antisense molecule, small interfering RNA (siRNA), protein, peptide, antibody, antigenic fragment, chemical compound or the like), which binds CIRP and inhibits (e.g., reduces, prevents, decreases, neutralizes) one or more biological activities of CIRP; or an agent that inhibits the expression of CIRP gene and/or protein or the release of bioactive CIRP. The term "biological activity of CIRP" refers to CIRP receptor binding, CIRP signaling, CIRP-mediated release of proinflammatory cytokines, CIRP-mediated inflammation and/or other CIRP-mediated activities. The term "antagonist" can be used interchangeably with the term "inhibitor".

The CIRP inhibitor can be an antibody, which binds and inhibits (e.g., reduces, prevents or neutralizes) one or more biological activities or functions of CIRP.

The antibody can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies, including fragments of chimeric, humanized, primatized, veneered or single chain antibodies. Functional fragments include antigen-binding fragments which bind to a mammalian CIRP. Such fragments can be produced by enzymatic cleavage or by recombinant techniques. For example, papain, pepsin or other protease with the requisite substrate specificity can also be used to generate fragments. Antibodies can also be produced in a variety of truncated forms using antibody genes in which one or more stop codons has been introduced upstream of the natural stop site.

Single chain antibodies, and chimeric, humanized or primatized (CDR-grafted), or veneered antibodies, as well as chimeric, CDR-grafted or veneered single chain antibodies, comprising fragments derived from different species, and the like are also encompassed by the present invention and the term "antibody". The various fragments of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Antibodies which are specific for a mammalian (e.g., human) CIRP can be raised against an appropriate immunogen, such as isolated and/or recombinant human protein of SEQ ID NO:1 or fragments thereof (including synthetic molecules, such as synthetic peptides). Antibodies can also be raised by immunizing a suitable host (e.g., mouse) with cells that express CIRP. In addition, cells expressing a CIRP can be used as immunogens or in a screen for antibody which binds CIRP.

Preparation of immunizing antigen, and polyclonal and monoclonal antibody production can be performed using any suitable technique. A variety of methods have been described (see e.g., Kohler et al., Nature, 256: 495-497 (1975) and Eur. J. Immunol. 6: 511-519 (1976); Milstein et al., Nature 266: 550-552 (1977), Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)).

Generally, a hybridoma is produced by fusing a suitable immortal cell line (e.g., a myeloma cell line such as SP2/0, P3X63Ag8.653 or a heteromyloma) with antibody producing cells. Antibody producing cells can be obtained from the peripheral blood or, preferably the spleen or lymph nodes, of humans or other suitable animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods which select recombinant antibody from a library (e.g., a phage display library), or which rely upon immunization of transgenic animals (e.g., mice) capable of producing a repertoire of human antibodies (see e.g., Jakobovits et al., Proc. Natl. Acad. Sci. USA, 90: 2551-2555 (1993); Jakobovits et al., Nature, 362: 255-258 (1993); Lonberg et al., U.S. Pat. No. 5,545,806; Surani et al., U.S. Pat. No. 5,545, 807; Lonberg et al., WO97/13852). Such immunization and isolation procedures are well known to one of ordinary skill in the art.

An antigenic fragment is a substance which when introduced into the body stimulates the production of an antibody. Antigens could include toxins, bacteria, foreign blood cells, and/or cells of transplanted organs.

A CIRP inhibitor can be a peptide (e.g., synthetic, recombinant, fusion or derivatized) which specifically binds to and inhibits (reduces, prevents, decreases, neutralizes) the activity of the CIRP. The peptide can be linear, branched or cyclic, e.g., a peptide having a heteroatom ring structure that includes several amide bonds. In a particular embodiment, the peptide is a cyclic peptide. The peptide refers to a compound consisting of from about 2 to about 100 amino acid residues wherein the amino group of one amino acid is linked to the carboxyl group of another amino acid by a peptide bond. Such peptides are typically less than about 100 amino acid residues in length and preferably are about 10, about 20, about 30, about 40 or about 50 residues.

Peptides that are selective for binding to a particular domain (e.g., unique domain) of a CIRP can be produced. A peptide can be, for example, derived or removed from a native protein by enzymatic or chemical cleavage, or can be synthesized by suitable methods, for example, solid phase peptide synthesis (e.g., Merrifield-type synthesis) (see, e.g., Bodanszky et al. "Peptide Synthesis," John Wiley & Sons, Second Edition, 1976). Peptides that are CIRP inhibitors can also be produced, for example, using recombinant DNA methodologies or other suitable methods (see, e.g., Sambrook J. and Russell D. W., Molecular Cloning: A Laboratory Manual, 3$^{rd}$ Edition, Cold Spring Harbor Laboratory Press, Cold Spring Harbor, N.Y., 2001).

CIRP inhibitors can also be fusion peptides fused, for example to a carrier protein (e.g., myc, his, glutathione sulfhydryl transferase) and/or tagged (e.g., radiolabeled, fluorescently labeled).

A peptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "Protecting Groups in Organic Synthesis", John Wiley and Sons, 1991. The functional groups of a peptide can also be derivatized (e.g., alkylated) using art-known methods.

Peptides can be synthesized and assembled into libraries comprising a few to many discrete molecular species. Such libraries can be prepared using methods of combinatorial chemistry, and can be screened using any suitable method to determine if the library comprises peptides with a desired biological activity. Such peptide inhibitors can then be isolated using suitable methods.

The polypeptide can comprise modifications (e.g., amino acid linkers, acylation, acetylation, amidation, methylation, terminal modifiers (e.g., cyclizing modifications)), if desired. The polypeptide can also contain chemical modifications (e.g., N-methyl-α-amino group substitution). In addition, the peptide inhibitor can be an analog of a known and/or naturally-occurring peptide, for example, a peptide analog having conservative amino acid residue substitution(s). These modifications can improve various properties of the peptide (e.g., solubility, binding), including its CIRP inhibiting activity.

A peptidomimetic refers to molecules which are not polypeptides, but which mimic aspects of their structures. Peptidomimetic antagonists can be prepared by conventional chemical methods (see e.g., Damewood J. R. "Peptide Mimetic Design with the Aid of Computational Chemistry" in Reviews in Computational Biology, 2007, Vol. 9, pp. 1-80, John Wiley and Sons, Inc., New York, 1996; Kazmierski W. K., "Methods of Molecular Medicine: Peptidomimetic Protocols," Humana Press, New Jersey, 1999). For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule, for example, with the amino acid(s) at or near the ligand binding site. For example, the binding moieties in a peptidomimetic can be the same as those in a peptide or protein inhibitor. The binding moieties can be an atom or chemical group which reacts with the receptor in the same or similar manner as the binding moiety in the peptide inhibitor. For example, computational chemistry can be used to design peptidemimetics of the CIRP binding to inhibit the activity of CIRP. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure.

This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more-CONH-groups for a-NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxy-acid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic inhibitors can then be isolated by suitable methods.

Other CIRP inhibitors like, for example, non-peptidic compounds or small molecules, can be found in nature (e.g., identified, isolated, purified) and/or produced (e.g., synthesized). Agents can be tested for CIRP binding specificity in a screen for example, a high-throughput screen of chemical compounds and/or libraries (e.g., chemical, peptide, nucleic acid libraries). Compounds or small molecules can be identified from numerous available libraries of chemical compounds from, for example, the Chemical Repository of the National Cancer Institute, the Molecular Libraries Small Molecules Repository (PubChem) and other libraries that are commercially available. Such libraries or collections of molecules can also be prepared using well-known chemical methods, such as well-known methods of combinatorial chemistry. The libraries can be screed to identify compounds that bind and inhibit CIRP. Identified compounds can serve as lead compounds for further diversification using well-known methods of medicinal chemistry. For example, a collection of compounds that are structural variants of the lead can be prepared and screened for CIRP binding and/or inhibiting activity. This can result in the development of a structure activity relationship that links the structure of the compounds to biological activity. Compounds that have suitable binding and inhibitory activity can be further developed for in vivo use. In one example, small molecule, $NaN_3$, inhibits CIRP transcription, as disclosed in "Oxygen-regulated expression of the RNA-binding proteins RBM3 and CIRP by HIF-1-independent mechanism", by S. Wellmann et al., *Journal of Cell Science*, 117, 1785-1794, 2004.

In some embodiments of the invention, the CIRP inhibitor has molecular weight less than 1000 Daltons.

CIRP inhibitors are also agents that inhibit (reduce, decrease, neutralize, prevent) the expression of a CIRP. Agents (molecules, compounds, nucleic acids, oligonucleotides) which inhibit CIRP gene expression (e.g., transcription, mRNA processing, translation) are effective CIRP inhibitors. Antisense oligonucleotides (e.g., DNA, riboprobes) can also be used as CIRP inhibitors to inhibit CIRP subunit expression. Antisense oligonucleotides are generally short (~13 to ~25 nucleotides) single-stranded nucleic acids which specifically hybridize to a target nucleic acid sequence (e.g., mRNA) and induce the degradation of the target nucleic acid (e.g., degradation of the RNA through RNase H-dependent mechanisms) or sterically hinder the progression of splicing or translational machinery. (See e.g., Dias N. and Stein C. A., *Mol. Can. Ther.* 1:347-355, 2002). There are a number of different types of antisense oligonucleotides that can be used as CIRP inhibitors including methylphosphonate oligonucleotides, phosphorothioate oligonucleotides, oligonucleotides having a hydrogen at the 2'-position of ribose replaced by an O-alkyl group (e.g., a methyl), polyamide nucleic acid (PNA), phosphorodiamidate morpholino oligomers (deoxyribose moiety is replaced by a morpholine ring), PN (N3'→P5' replacement of the oxygen at the 3' position on ribose by an amine group) and chimeric oligonucleotides (e.g., 2'-O-Methyl/phosphorothioate).

Antisense oligonucleotides can be designed to be specific for a CIRP using predictive algorithms. (See e.g., Ding, Y., and Lawrence, C. E., *Nucleic Acids Res.*, 29:1034-1046, 2001; Sczakiel, G., *Front. Biosci.*, 5:D194-D201, 2000; Scherr, M., et al., *Nucleic Acids Res.*, 28:2455-2461, 2000; Patzel, V., et al. *Nucleic Acids Res.*, 27:4328-4334, 1999; Chiang, M. Y., et al., *J. Biol. Chem.*, 266:18162-18171, 1991; Stull, R. A., et al., *Nucleic Acids Res.*, 20:3501-3508, 1992; Ding, Y., and Lawrence, C. E., *Comput. Chem.*, 23:387-400, 1999; Lloyd, B. H., et al., *Nucleic Acids Res.*, 29:3664-3673, 2001; Mir, K. U., and Southern, E. M., *Nat. Biotechnol.*, 17:788-792, 1999; Sohail, M., et al., *Nucleic Acids Res.*, 29:2041-2051, 2001; Altman, R. K., et al., *J. Comb. Chem.*, 1:493-508, 1999). The antisense oligonucleotides can be produced by suitable methods; for example, nucleic acid (e.g., DNA, RNA, PNA) synthesis using an automated nucleic acid synthesizer (from, e.g., Applied Biosystems) (see also Martin, P., *Helv. Chim. Acta* 78:486-504, 1995). Antisense oligonucleotides can also be stably expressed in a cell containing an appropriate expression vector.

Antisense oligonucleotides can be taken up by target cells via the process of adsorptive endocytosis. Thus, in the treatment of a subject (e.g., mammalian), antisense CIRP can be delivered to target cells by, for example, injection or infusion. For instance, purified oligonucleotides or siRNA/shRNA, can be administered alone or in a formulation with a suitable drug delivery vehicle (e.g., liposomes, cationic polymers, (e.g., poly-L-lysine' PAMAM dendrimers, polyalkylcyanoacrylate nanoparticles and polyethyleneimine) or coupled to a suitable carrier peptide (e.g., homeotic transcription factor, the Antennapedia peptide, Tat protein of HIV-1, E5CA peptide).

Methods of identifying an antagonist agent (e.g., an antibody) against CIRP will be described below.

A composition comprising a CIRP can be used in a binding assay to detect and/or identify agents that can bind to the CIRP including antibodies of the invention.

Compositions suitable for use in a binding assay include, for example, cells which naturally express a mammalian CIRP or functional variant thereof and recombinant cells expressing a mammalian CIRP or functional variant thereof. Compositions suitable for use in a binding assay also include, membrane preparations which comprise a mammalian CIRP or functional variant thereof. Such membrane preparations can contain natural (e.g., plasma membrane) or synthetic membranes. Preferably, the membrane preparation is a membrane fraction of a cell that contains a mammalian CIRP or a functional variant thereof.

In one embodiment, the method of detecting or identifying agent (e.g., an antibody) that binds to a mammalian CIRP is a competitive binding assay in which the ability of a test agent (e.g. an antibody) to inhibit the binding of a reference agent (e.g., a ligand or another antibody of known specificity) is assessed. For example, the reference agent can be labeled with a suitable label as described below, and the amount of labeled reference agent required to saturate the CIRP present in the assay can be determined. A saturating amount of labeled reference agent and various amounts of a test agent can be contacted with a composition comprising a mammalian CIRP or functional variant thereof under conditions suitable for binding and complex formation determined. The specificity of the formation of the complex between the CIRP and the test agent can be determined using a suitable control (e.g., unlabeled agent, label alone).

The formation of a complex between either the reference or a test agent and the CIRP or fragments thereof including immunogenic peptides as described above can be detected or measured directly or indirectly using suitable methods. For example, the agent can be labeled with a suitable label and the formation of a complex can be determined by detection of the label. The specificity of the complex can be determined using a suitable control such as unlabeled agent or label alone. Labels suitable for use in detection of a complex between an agent and a mammalian CIRP or functional variant thereof include, for example, a radioisotope, an epitope, an affinity label (e.g., biotin, avidin), a spin label, an enzyme, a fluorescent group or a chemiluminescent group.

With respect to a competitive binding assays used to determine the ability of a test agent such as an antibody to bind an CIRP, such ability can be reported as the concentration of test agent required for 50% inhibition ($IC_{50}$ values) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents which are suitable for use in the method include molecules and compounds which specifically bind to a mammalian CIRP or a functional variant thereof, for example, a ligand of CIRP or an antibody. Preferred reference agents are antibodies having a known specificity against the fragments of the human CIRP (SEQ ID NO:1).

An agent which binds a CIRP can be further studied to assess the ability of that agent to inhibit (e.g., reduce, prevent, neutralize) one or more "biological activities of CIRP". As defined previously term "biological activity of CIRP" refers to CIRP receptor binding, CIRP signaling, CIRP-mediated release of proinflamatory cytokines, CIRP-mediated inflammation and/or other CIRP-mediated activities. Thus, assays detecting these CIRP-mediated functions can be used to evaluate the inhibition activity of a test agent (e.g., the ability of a test agent to inhibit one or more functions of CIRP).

Assessment of whether an agent (e.g., an antibody) inhibits a biological activity of a CIRP can be performed, for example, by determining whether an antibody inhibits release of a proinflammatory cytokine from a mammalian cell. Examples of suitable cytokines include TNF, IL-6 or HMGB1.

For these methods, the cell can be any cell that can be induced to produce a proinflammatory cytokine. The cell is an immune cell, for example macrophages, monocytes, or neutrophils.

Figure 4:
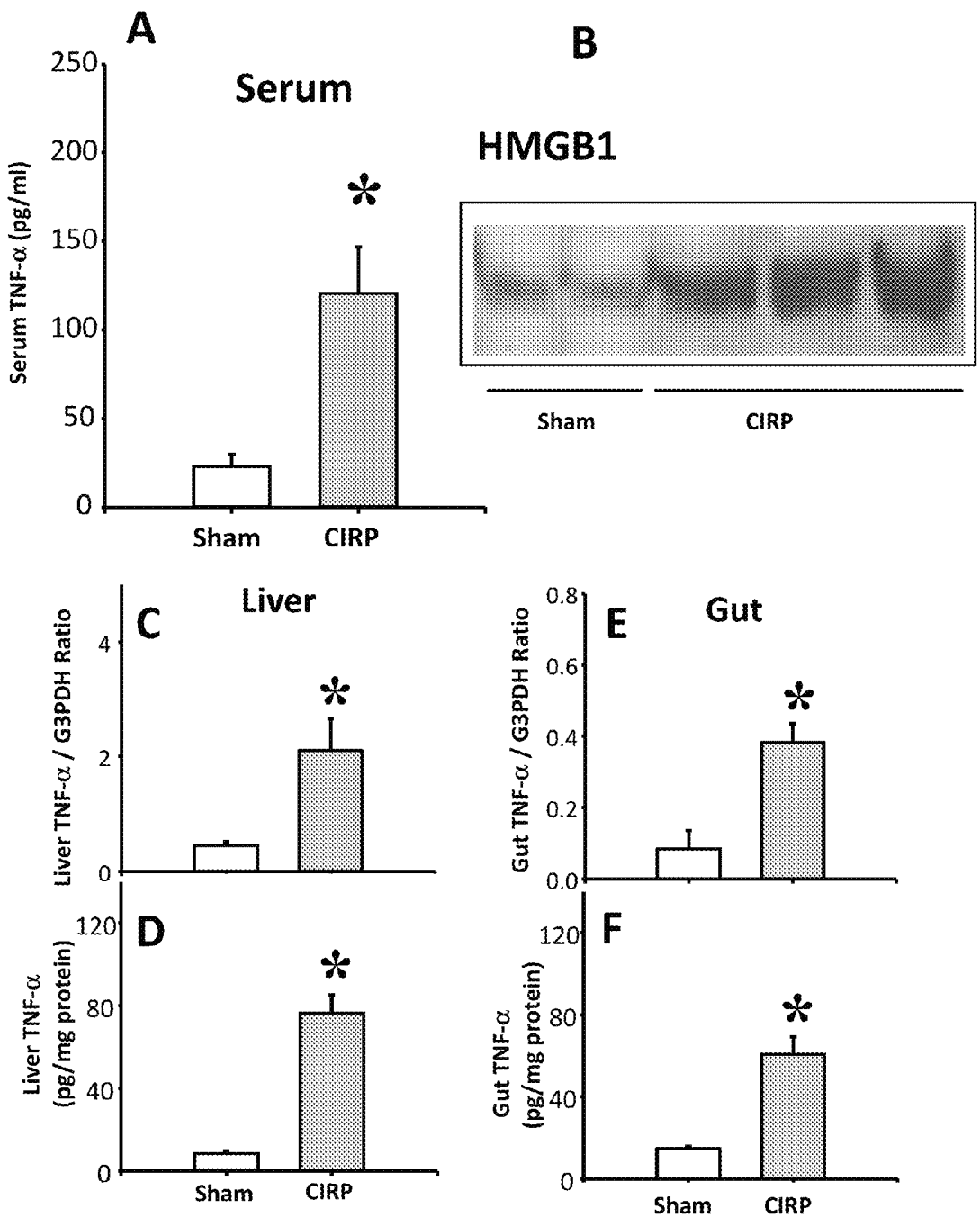
FIG. 4 is illustrates the increase in TNF and HMGB1 in blood, liver and gut after administration of rCIRP.
Figure 8:
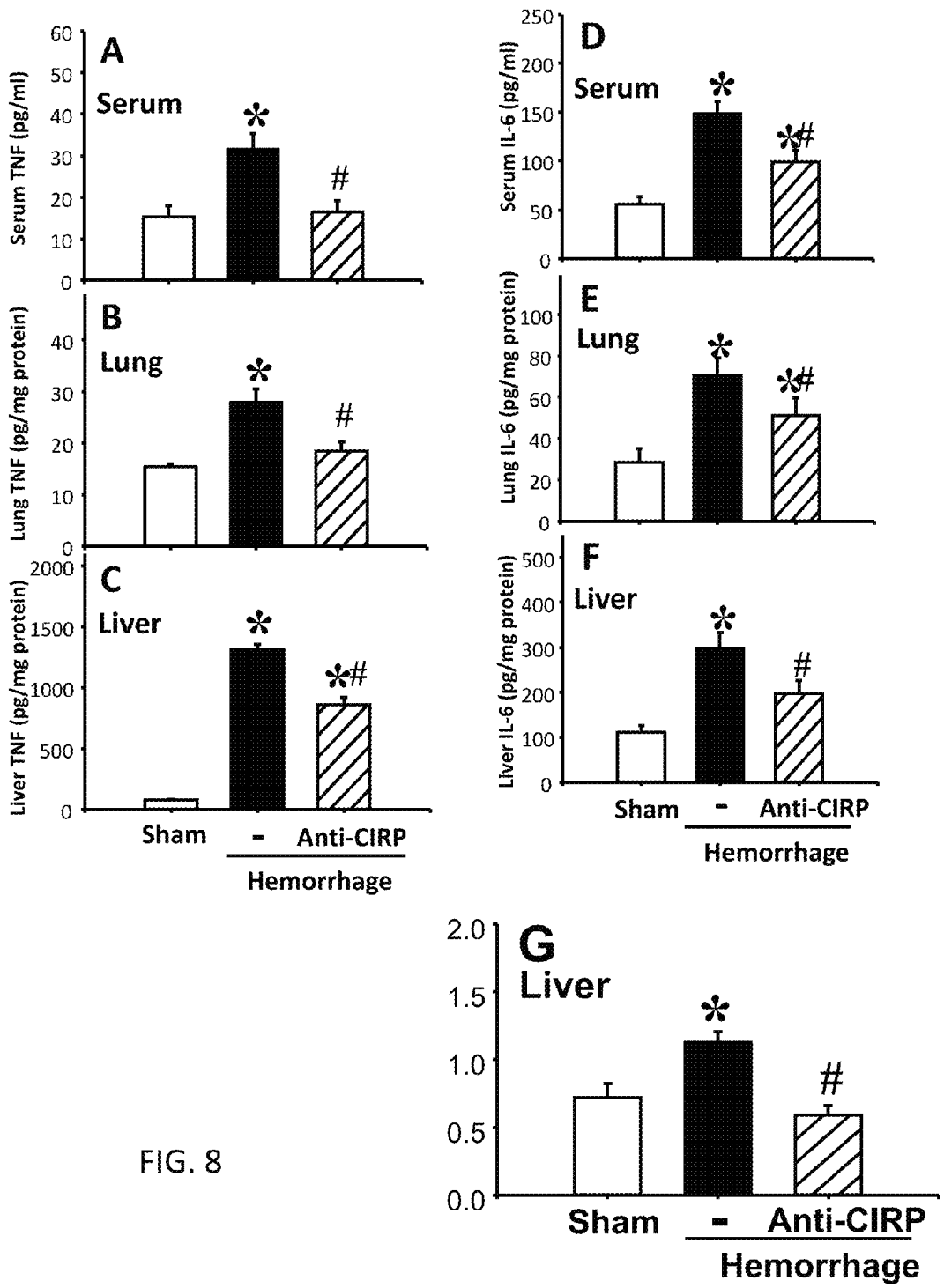
FIG. 8 consists of graphs illustrating the reduction of serum, lung and liver IL-6 by anti-CIRP antibodies in animal models of hemorrhage after administration of anti-CIRP antibody, compared with untreated control.

Evaluation of the inhibition of cytokine production can be by any means known, including quantitation of the cytokine (e.g., with ELISA), or by bioassay, (e.g. determining whether proinflammatory cytokine activity is reduced), or by measurement of the proinflammatory cytokine mRNA. The skilled artisan could utilize any of these assays without undue experimentation. For non-limiting Examples on inhibition of the release of proinflamatory cytokine by the CIRP inhibiting agents see FIGS. 4 and 8. FIG. 8A shows reduction of serum TNF by treatment with anti-CIRP antibodies in an animal model of hemorrhage compared with untreated controls. Reduction of tissue TNF by treatment with anti-CIRP antibodies in an animal model of hemorrhage compared with untreated controls is shown in FIG. 8B-C. FIG. 8D-F shows reduction in IL-6 (e.g., serum, lung and liver IL-6) by treatment with anti-CIRP antibodies in an animal model of hemorrhage compared with untreated controls.

Another way of measuring proinflammatory cytokine release involves treating the mammalian cell with an antibody along with an agent that stimulates a proinflammatory cytokine cascade. A preferred agent is bacterial lipopolysaccharide (LPS). The compound can be administered to the mammalian cell either before the agent, at the same time as the agent, or after the agent. Preferably, the compound is administered before the agent. See, e.g., U.S. Pat. No. 6,610,713, the relevant teachings of which are incorporated herein by reference.

Figure 7:
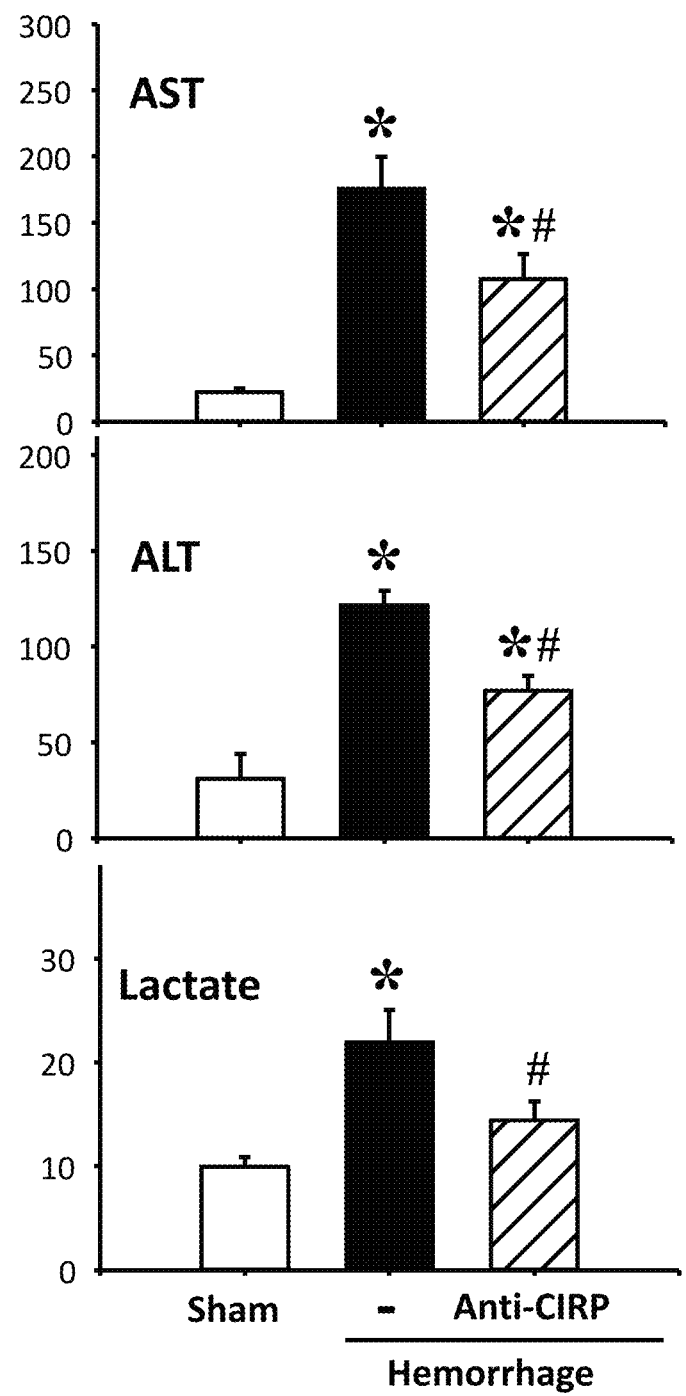
FIG. 7 is a set of graphs illustrating the reduction of serum AST, ALT and lactate after administration of an anti-CIRP antibody composition in animals models of hemorrhage compared with untreated control.

Other biological activities of CIRP that can be measured to assess CIRP inhibition include AST levels in animal models, liver MPO levels in animal models and lactate levels in animal models. The levels of those markers are commonly elevated during an inflammatory response. Inhibitors of biological activities of CIRP can reduce the levels of one or more of these markers in animal models undergoing inflammatory response relative to untreated controls. Methods for assessing inhibition of the release of these markers by the CIRP inhibiting agent are given in FIG. 7A-C in Exemplification section. The inhibitory effects of anti-CIRP antibodies on AST levels, in an animal model of hemorrhage compared with untreated controls, is described in FIG. 7A. FIG. 8G depicts reduction of liver MPO levels by treatment with anti-CIRP antibodies in an animal model of hemorrhage compared with untreated controls. In FIG. 7B-C, the reduction of serum ALT and lactate by the anti-CIRP antibodies is given.

These methods can be performed in vivo, where an animal, e.g., a rat, is treated with the compound along with an agent that stimulates a proinflammatory cytokine cascade, and the effect of the agent on induction of the proinflammatory cytokine cascade is measured, e.g., by measuring serum TNF levels. However, due to the relative ease of doing these types of assays with cell cultures rather than with whole animals, the methods are preferably performed in vitro, for example using macrophage cultures.

Methods of Therapy

As used herein, an "inflammatory disease or condition" refers to a disease or condition that causes increased inflammation in an individual. An inflammatory disease or condition also refers to an infectious disease or condition that causes increased inflammation in an individual. The inflammatory disease or condition can be a "chronic inflammatory disease or condition". A chronic inflammatory disease or condition is an inflammatory condition that does not resolve after a period of weeks, months or longer. Chronic inflammatory conditions can follow an acute inflammatory condition, or for some diseases or conditions can occur in the absence of an acute inflammatory disease or condition. Alternatively, an inflammatory condition can be a consequence of an acute inflammatory episode. An "acute inflammatory episode," as used herein, refers to an increased immune response. Symptoms of acute inflammation include redness, heat, swelling, pain, and loss of function, e.g., loss of joint movement. For example, an acute inflammatory episode of a chronic inflammatory disease or condition differs from the typical symptoms of a chronic inflammatory disease or condition in the following ways. Frequently, during an acute inflammatory response the liver synthesizes acute phase proteins or acute phase reactants that are detectable in the blood stream. Acute phase reactants include C-reactive protein (CRP); alpha 1-antitrypsin; alpha 1-antichymotrypsin; alpha 2-macroglobulin; coagulation factors such as fibrinogen, fibrin, prothrombin, thrombin, factor VIII, and plasminogen; complement proteins, and serum amyloid protein. In addition, during an acute inflammatory episode, local inflammatory cells, e.g., neutrophils and macrophages, secrete a number of cytokines into the bloodstream, most notably IL-1, IL-6, IL-11, HMGB1 and TNF-alpha ("the cytokine cascade"). CIRP inhibitors may be administered to inhibit, reduce or otherwise ameliorate some or all of these agents and markers of inflammatory conditions.

Nonlimiting examples of inflammatory conditions which can be usefully treated using the present invention are selected from the group consisting of appendicitis, peptic, gastric and duodenal ulcers, peritonitis, pancreatitis, Crohn's disease, ulcerative colitis, ileus, epiglottitis, achalasia, cholangitis, cholecystitis, hepatitis, Whipple's disease, asthma, allergy, anaphylactic shock, immune complex disease, organ ischemia-reperfusion injury, organ necrosis, hay fever, sepsis, sepsis-septic scock, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumoultramicroscopic silicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, vasulitis, angiitis, endocarditis, arteritis, atherosclerosis, thrombophlebitis, pericarditis, myocarditis, ischemia, periarteritis nodosa, rheumatic fever, coeliac disease, adult respiratory distress syndrome, chronic obstructive pulmonary disease, meningitis, encephalitis, neuritis, neuralgia, spinal cord injury, paralysis, uveitis, arthritides, arthralgias, osteomyelitis, fasciitis, Paget's disease, gout, periodontal disease, arthritis, synovitis, myasthenia gravis, thryoiditis, systemic lupus erythematosus, allograft rejection, graft-versus-host disease, Goodpasture's syndrome, Behcets's syndrome, ankylosing spondylitis, Berger's disease, Retier's syndrome, Hodgkins disease, psoriasis, myocardial infraction, stroke, inflammatory bowel disease, necrotizing enterocolitis and trauma-hemorrhage.

In another embodiment, the inflammatory condition is selected from the group consisting of appendicitis, peptic, gastric and duodenal ulcers, peritonitis, pancreatitis, hepatitis, asthma, allergy, anaphylactic shock, organ necrosis, hay fever, sepsis, sepsis-septic shock, septicemia, endotoxic shock, Crohn's disease, ulcerative colitis, ileus, cachexia, septic abortion, disseminated bacteremia, coeliac disease, adult respiratory distress syndrome, chronic obstructive pulmonary disease, arthritis, systemic lupus erythematosus, allograft rejection, graft-versus-host disease, spinal cord injury, paralysis, psoriasis, ischemia-reperfusion of gut, liver, kidneys, heart, brain and limbs, myocardial infraction, stroke, inflammatory bowel disease, necrotizing enterocolitis and trauma-hemorrhage.

In another embodiment, the inflammatory condition is selected from the group consisting of peritonitis, pancreatitis, sepsis, sepsis-septic shock, endotoxic shock, Crohn's disease, ulcerative colitis, ileus, adult respiratory distress syndrome, chronic obstructive pulmonary disease, rheumatoid arthritis, systemic lupus erythematosis, ischemia-reperfusion of gut, liver, kidneys, heart, brain and limbs, myocardial infraction, stroke, inflammatory bowel disease, necrotizing enterocolitis, asthma and trauma-hemorrhage.

Alternatively, the inflammatory condition is selected from the group consisting of trauma-hemorrhage, sepsis-septic shock, ischemia-reperfusion of gut, liver, kidneys, heart, brain and limbs, myocardial infraction, stroke, inflammatory bowel disease and necrotizing enterocolitis.

Modes of Administration

The route of administration of the CIRP inhibitor depends on the condition to be treated. For example, intravenous injection may be preferred for treatment of a systemic disorder such as septic shock, and oral administration may be preferred to treat a gastrointestinal disorder such as a gastric ulcer.

According to the method, one or more CIRP inhibitors of the present invention can be administered to the subject by an appropriate route, either alone or in combination with another drug. An effective amount of an agent (i.e. a CIRP inhibitor) is administered. An "effective amount" is an amount sufficient to achieve the desired therapeutic or prophylactic effect, under the conditions of administration, such as an amount sufficient for inhibition of an inflammatory response and alleviating or curing an inflammatory condition. The agents can be administered in a single dose or multiple doses. The dosage can be determined by methods known in the art and is dependent, for example, upon the particular agent chosen, the subject's age, sensitivity and tolerance to drugs, and overall well-being. Suitable dosages for antibodies can be from about 0.01 mg/kg to about 100 mg/kg body weight per treatment.

A variety of routes of administration are possible including, for example, oral, dietary, topical, transdermal, rectal, parenteral (e.g., intravenous, intraarterial, intramuscular, subcutaneous injection, intradermal injection), and inhalation (e.g., intrabronchial, intranasal or oral inhalation, intranasal drops) routes of administration, depending on the agent and disease or condition to be treated. Administration can be local or systemic as indicated. The preferred mode of administration can vary depending upon the particular agent (CIRP inhibitor) chosen, and the particular condition (e.g., disease) being treated. Intravenous, oral or parenteral administration are preferred.

The agent can be administered as a neutral compound or as a pharmaceutically acceptable salt. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

As used herein, a "pharmaceutically acceptable salt" of a disclosed compound is an ionic bond-containing product of reacting a compound of the invention with either an acid or a base, suitable for administering to a subject. For example, an acid salt of a compound containing an amine or other basic group can be obtained by reacting the compound with a suitable organic or inorganic acid, such as hydrogen chloride, hydrogen bromide, acetic acid, perchloric acid and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. Salts can also be formed with suitable organic bases when the compound comprises an acid functional group such as —COOH or —SO$_3$H. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl)aminomethane and the like.

The agent can be administered to the individual as part of a pharmaceutical composition comprising an inhibitor of CIRP and a pharmaceutically acceptable carrier.

As used herein, a "pharmaceutical composition" is a formulation comprising the disclosed CIRP antagonist (such as an anti-CIRP antibody) and a pharmaceutically acceptable diluent or carrier, in a form suitable for administration to a subject. Suitable pharmaceutically acceptable carriers include inert solid fillers or diluents and sterile aqueous or organic solutions. Formulation will vary according to the route of administration selected (e.g., solution, emulsion, capsule). Suitable pharmaceutical carriers can contain inert ingredients which do not interact with the promoter (agonist) or inhibitor (antagonist) of CIRP. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of the disclosed compound or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration.

As used herein, a "subject" includes mammals, e.g., humans, companion animals (e.g., dogs, cats, birds and the like), farm animals (e.g., cows, sheep, pigs, horses, fowl and the like) and laboratory animals (e.g., rats, mice, guinea pigs and the like). In a preferred embodiment of the disclosed methods, the subject is human.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes).

Preferred embodiments of the invention are described in the following Examples. Other embodiments within the scope of the claims herein will be apparent to one skilled in the art from consideration of the specification or practice of the invention as disclosed herein. It is intended that the specification, together with the Examples, be considered exemplary only, with the scope and spirit of the invention being indicated by the Claims which follow the Example.

EXEMPLIFICATION

Materials and Methods

Experimental Animals:

Male Sprague-Dawley rats (275-325 g in body weight) were obtained from Charles River Laboratories (Wilmington, Mass.), and were housed in a temperature-controlled room on a 12-h light/dark cycle and fed on a standard Purina rat chow diet. Prior to the induction of hemorrhage shock, rats were fasted overnight but allowed water ad libitum. The experiments were performed in accordance with the National Institutes of Health guidelines for the use of experimental animals. This project was approved by the Institutional Animal Care and Use Committee (IACUC) of The Feinstein Research Institute for Medical Research.

Animal Model of Hemorrhage Shock:

The model of hemorrhage shock used in this experiment was described in detail previously with minor modification (Wang P, Hauptman J G, Chaudry I H: Hemorrhage produces depression in microvascular blood flow which persists despite fluid resuscitation. *Circ Shock* 32:307-318, 1990; Wu R, Dong W, Zhou M, Cui X, Simms H H, Wang P: A novel approach to maintaining cardiovascular stability after hemorrhagic shock: beneficial effects of adrenomedullin and its binding protein. *Surgery* 137:2005). Briefly, rats were anesthetized with isoflurane inhalation. Catheters (PE-50 tubing) were placed in a femoral vein and artery after carefully separating the femoral nerve and blood vessels. The femoral artery on the opposite side was also catheterized. One arterial catheter was used for monitoring the mean arterial pressure (MAP) and heart rate (HR) via a blood pressure analyzer (Digi-Med, Louisville, Ky.), the other was for blood withdrawal and the venous catheter was used for fluid resuscitation. The rat was bled to an MAP of 40 mmHg within 10 min. This pressure was maintained for 90 min by further withdrawal of small volumes of blood or provision of small volumes of lactated Ringer's solution. At the end of this hypotensive period, the rats were then resuscitated with lactated Ringer's solution (equivalent 4 times the maximum bleed-out volume, which was approximately 60% of calculated blood volume) over a 60-min period. The shed blood was not used for resuscitation and the animals were not heparinized prior to, during, or following hemorrhage. After 4 h, blood samples were collected and placed on ice to allow clotting. The samples then were centrifuged at 1200 g for 10 min at 4° C., and the serum samples were stored at −80° C. until assayed. Tissues samples were also collected and saved to liquid nitrogen immediately, then stored at −80° C. until assayed. Sham-operated animals underwent the same surgical procedure but were neither bled nor resuscitated.

Recombinant Protein (rCIRP):

We have used a serial method for expression and purification of recombinant proteins with a hexahistidine tag (His-tag) from bacterial expression systems. The cDNA was prepared by reverse transcribing 4 µg of total tissue RNA of rat heart using a modified oligo d ($T_{16}$) primer with 50 U MuLV reverse transcriptase as described previously (Dwivedi A J, Wu R, Nguyen E, Higuchi S, Wang H, Krishnasastry K, Marini C P, Ravikumar T S, Wang P: Adrenomedullin and adrenomedullin binding protein-1 prevent acute lung injury after gut ischemia-reperfusion. *J Am Coll Surg* 205:284-293, 2007). To obtain CIRP protein, the CIRP coding sequence was amplified by PCR from CIRP cDNA with a primer set: sense 5'-CAC CAT GGC ATC AGA TGA AGG-3' (SEQ ID No. 2) and antisense 5'-CTC GTT GTG TGT AGC ATA GC-3' (SEQ ID No. 3) were synthesized (design according to GenBank: NM_031147, NCBI) and used to isolate the rat CIRP clone. The PCR product was then digested with EcoRV and NotI and cloned into pENTR vector, the C-terminal hexa-histidine tag (His-tag) system (as described by Invitrogen), and then transformed to *E. coli* BL21 (DE3), as a resulting expression plasmid. Induced expression of CIRP performed in several liters of BL21 (DE3) cell cultures and then CIRP was isolated and purified as described by the manufacturer (Novagen, Madison, Wis.). To avoid any inadvertent lipopolysaccharide (LPS) contamination, we used Triton X-114 extraction to remove possible endotoxin contamination, and final LPS content was determined using the Limulus amebocyte lysate (LAL) assay (BioWhittaker Inc, Walkersville, Md.) as described previously (Ertel W, Morrison M H, Wang P, Ba Z F, Ayala A, Chaudry I H: The complex pattern of cytokines in sepsis. Association between prostaglandins, cachectin, and interleukins. *Ann Surg* 214:141-148, 1991).

Administration of rCIRP:

In additional groups of health normal animals, rCIRP (1 mg/kg BW) or buffer (same volume, 1 ml) were administered. At 4 h after the completion of treatment, blood samples were collected and placed on ice to allow clotting, and then were centrifuged at 1200 g for 10 min at 4° C., and the serum samples were stored at −80° C. until assayed. And also, tissue samples were collected and saved to liquid nitrogen immediately, then were stored at −80° C. until assayed. In another groups of hemorrhagic animals, antibody against CIRP (3 mg/kg BW) or buffer (same volume, 1 ml) were administered at 15 min after the beginning of resuscitation in hemorrhaged animals via the femoral venous catheter over a period of 45 min. At 1.5 h after the completion of treatment, tissues or blood samples were collected same above.

Anti-CIRP Antibody Production:

Polyclonal antiserum against CIRP was produced following standard procedures by injecting rabbits with the purified recombinant CIRP at intervals of three or more weeks (Covance Research Products, Denver, Pa.). The IgG of anti-CIRP antibody was affinity purified from serum by using immobilized immunopure protein-A/G column, according to the supplier's instructions (Pierce, Rockford, Ill.). Antibody titers were determined by a direct ELISA in 96-well format (as described by Covance Research Products, Denver, Pa.). LPS was not detectable in the purified antibody preparations as measured by Limulus amebocyte lysate assay (BioWhittaker).

Determination of CIRP Gene Expression:

To examine whether the expression of the CIRP gene is altered in hemorrhage, hemorrhagic tissues were determined and quantified by real-time reverse transcription-polymerase chain reaction (RT-PCR). Q-PCR will be carried out on cDNA samples reverse transcribed from 4 µg RNA using murine leukemia virus reverse transcriptase (Applied Biosystems). Using the QuantiTect SYBR Green PCR kit (Qiagen, Valencia, Calif.), reactions will be carried out in 24 µl final volumes containing 2 pmol of forward and reverse primers, 12 µl QuantiTect Master Mix, and 1 µl cDNA. Amplification will be performed according to Qiagen's recommendations with an Applied Biosystems 7300 real-time PCR. Expression amount of rat G3PDH mRNA will be used for normalization of each sample, and analysis of each specific mRNA will be conducted in duplicate. Relative expression of mRNA will be calculated by the ΔΔCt-method, and results expressed as fold change with respect to the corresponding experimental control. The following rat primers will be used: CIRP (NM_031147): 5'-GGG TCC TAC AGA GAC AGC TAC GA-3' (forward), (SEQ ID No. 4), 5'-CTG GAC GCA GAG GGC TTT TA-3' (reverse), (SEQ ID No. 5); G3PDH (XM_579386): 5'-ATG ACT CTA CCC ACG GCA AG-3' (forward), (SEQ ID No. 6), 5'-CTG GAA GAT GGT GAT GGG TT-3' (reverse), (SEQ ID No. 7). Gene expression of TNF-α was assessed using RT-PCR. The primers for TNF-α and housekeeping genes were as follows: rat TNF-α, 5'CCC AGA CCC TCA CAC TCA GA 3', (SEQ ID No. 8), 5'GCC ACT ACT TCA GCA TCT CG 3'(SEQ ID No. 9) and G3PDH, 5'TGA AGG TCG GTG TCA ACG GAT TTG GC 3' (SEQ ID No. 10), 5'CAT GTA GGC CAT GAG GTC CAC CAC 3' (SEQ ID No. 11) as previously described (Wu R, Zhou M, Wang P: Adrenomedullin and adrenomedullin binding protein-1 downregulate TNF-alpha in macrophage cell line and rat Kupffer cells. *Regul Pept* 112:19-26, 2003).

Western Blot Analysis:

Expression of CIRP protein in the serum and tissue were determined using rabbit polyclonal antibody against CIRP (ProteinTech Group, Chicago, Ill.) by western blot analysis. Briefly, equal amounts of serum (volume) and tissue homogenates (protein mg/lane) were fractionated on 4-12% NuPAGE Bis-Tris gels (Invitrogen, Carlsbad, Calif.) and transferred to nitrocellulose membrane, then were blocked by incubation in TBST buffer (10 mM Tris-HCl [pH 7.5], 150 mM NaCl, 0.1% Tween 20) containing 5% nonfat dry milk for 1 h room temperature. The membrane was incubated with rabbit polyclonal antibodies overnight at 4° C. Following several times washed in TBST buffer and incubated with horseradish peroxidase-linked anti-rabbit IgG (Cell Signaling Technology, Danvers, Mass.), a chemiluminescent peroxidase substrate (ECL; GE Healthcare Bio-Sciences, Piscataway, N.J.) was applied according to the manufacturer's instructions, and the membranes were exposed to X-ray film. Western blots results were scanned and the relative band intensity was quantified by using the GS800 Calibrated Densitometer, Bio-Rad Image Analysis Systems (Hercules, Calif.). Anti-β-actin antibody (for cytoplasmic protein, Santa Cruz Biotechnology) was used to ensure equal loading. The levels of HMGB1 in rat serum were measured using rabbit polyclonal anti-HMGB1 antibody as previously described (Wang H, Bloom O, Zhang M, Vishnubhakat J M, Ombrellino M, Che J, Frazier A, Yang H, Ivanova S, Borovikova L, Manogue K R, Faist E, Abraham E, Andersson J, Andersson U, Molina P E, Abumrad N N, Sama A, Tracey K J: HMG-1 as a late mediator of endotoxin lethality in mice. *Science* 285:248-251, 1999).

Cell Culture:

Murine macrophage-like RAW 264.7 cells were obtained from ATCC (American Type Culture Collection, Manassas, Va.), and were grown in Dulbecco's Modified Eagle's Medium (DMEM, Life Technologies, Grand Island, N.Y.) containing 10% (vol/vol) FBS (heat-inactivated at 56° C. for 30 min), 100 U/ml penicillin, 100 µm/ml streptomycin and 2 mM glutamine. Cells were re-suspended in medium and incubated in 6 or 48-well tissue-culture plates overnight in a humidified incubator (37° C., 5% $CO_2$). In the experiments, cell monolayers were stimulated with or without recombinant CIRP at various indicated concentrations and for various indicated times. The cell-free supernatants were assayed for TNF-α by ELISA or for HMGB1 by western blot analysis.

Inflammatory Cytokine Assay:

As an index of the inflammatory cytokine cascade and the acute inflammatory response, supernatants from cells incubated with recombinant CIRP were measured for TNF-α and IL-6 levels using a commercially available enzyme-linked immunosorbent assay (ELISA) kits (BioSource International, Camarillo, Calif.) according to the manufacturer's instruction. To quantify TNF-α and IL-6 protein levels in serum and tissue, we harvested serum samples 4 h after hemorrhage, or 4 h after treatment with recombinant CIRP from animals by cardiac puncture at the time that the rats were sacrificed, and collected tissue samples, and carried out by the same method as above.

Determination of Serum Levels of Transaminases and Lactate:

Serum concentrations of aspartate aminotransferase (AST), alanine aminotransferase (ALT), and lactate were determined by using assay kits according to the manufacturer's instructions (Pointe Scientific, Lincoln Park, Mich.).

Granulocyte Myeloperoxidase Assessment:

Neutrophil accumulation within the pulmonary and hepatic tissues was estimated using the myeloperoxidase (MPO) activity assay as previously reported (Dwivedi A J, Wu R, Nguyen E, Higuchi S, Wang H, Krishnasastry K, Marini C P, Ravikumar T S, Wang P: Adrenomedullin and adrenomedullin binding protein-1 prevent acute lung injury after gut ischemia-reperfusion. *J Am Coll Surg* 205:284-293, 2007).

Statistical Analysis:

All data are expressed as means±SE and compared by one-way analysis of variance (ANOVA) and Student-Newman-Keuls' method. The survival rate was estimated by Kaplan-Meier method and compared the log-rank test. Differences in values were considered significant if $P<0.05$.

Results

Alteration in the Circulating and Tissue Levels of CIRP after Hemorrhage:

Rats that underwent an experimental blood loss (hemorrhage) show significantly increased expression of CIRP mRNA in various tissues. CIRP expression increased by ~5 fold in the liver (FIG. 2A) and ~3 fold in the heart (FIG. 2B) as compared to sham-operated controls. High circulating levels of CIRP protein were detected by Western blot analysis in the hemorrhagic rats. The hemorrhage group showed a clear immunoreactive CIRP band, which was not found in sham group (FIG. 2C). The expression of CIRP protein also increased in the heart of the hemorrhaged animals (FIG. 2D), compared with sham-operated rats (β-actin was to ensure equal loading).

Figure 3:
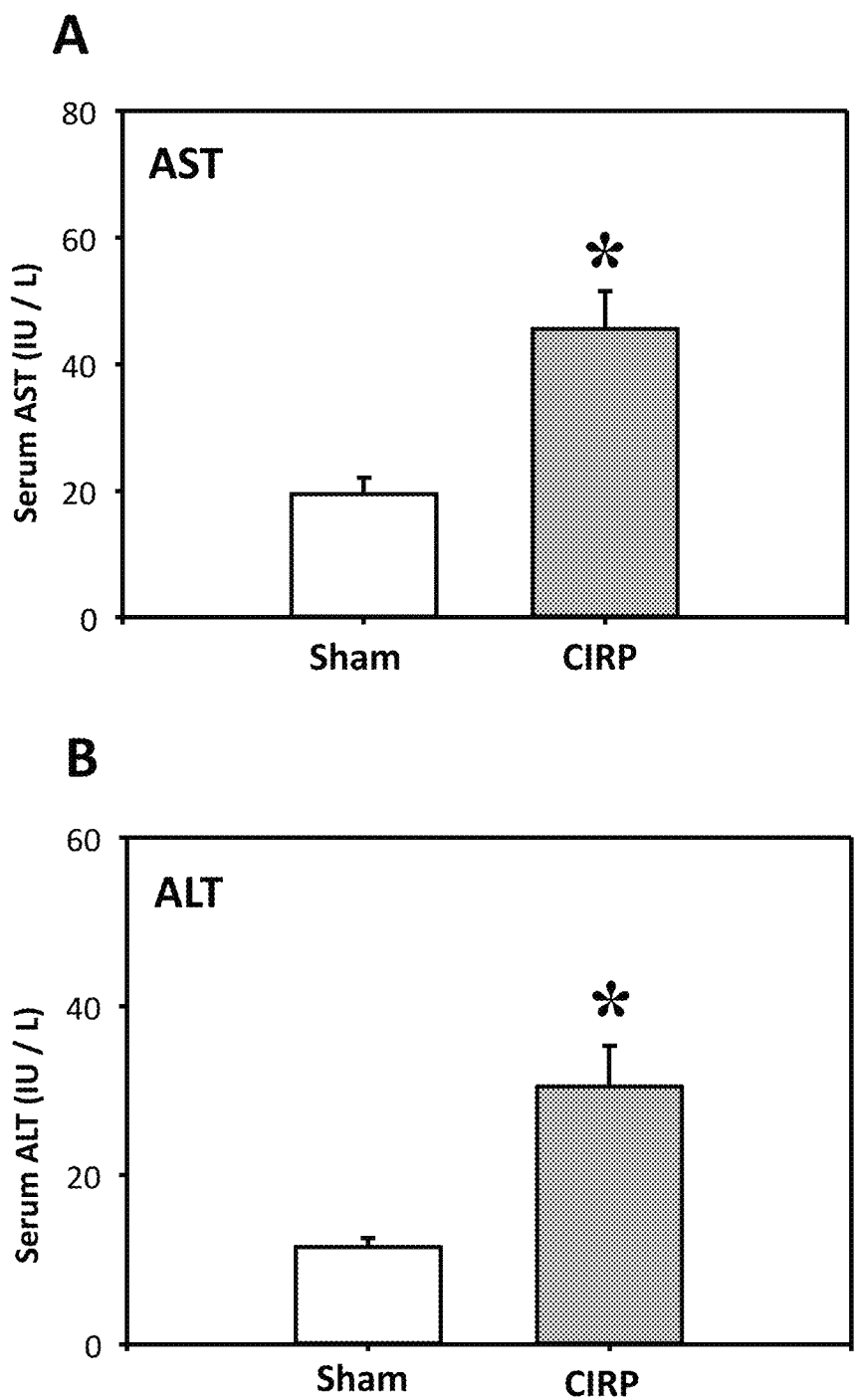
FIG. 3 is a pair of graphs illustrating the elevation of AST and ALT after administration of recombinant CIRP (rCIRP).

Recombinant CIRP (rCIRP) Induces Tissue Injury in Healthy Rats:

To investigate the effect of rCIRP in normal animals, we administrated rCIRP (1 mg/kg BW), a recombinant protein purified from bacterial expression systems, to normal healthy rats, and measured serum levels of AST and ALT (indicators of liver injury). The rats treated with rCIRP showed significantly elevated levels of AST (FIG. 3A) and ALT (FIG. 3B). These results show that rCIRP directly causes inflammatory tissues injury.

Recombinant CIRP (rCIRP) Increases Proinflammatory Cytokine Levels in Healthy Rats:

After the injection of rCIRP (1 mg/kg BW) or buffer solution (same volume), as control, serum levels of TNF-α increased markedly in the rCIRP group, ~5 fold higher than buffer (sham) group (FIG. 4A). Both TNF-α gene and protein expression increased in the liver (FIGS. 4C and D) and gut (FIGS. 4E and F) after rCIRP administration. FIG. 4B shows an increase in the circulating level of HMGB1, a proinflammatory cytokine, after administration of rCIRP (1 mg/kg BW). rCIRP-treated rats showed intense immunoreactive HMGB1 bands (in triplicate), as compared to weak bands in sham group (in duplicate).

Figure 5:
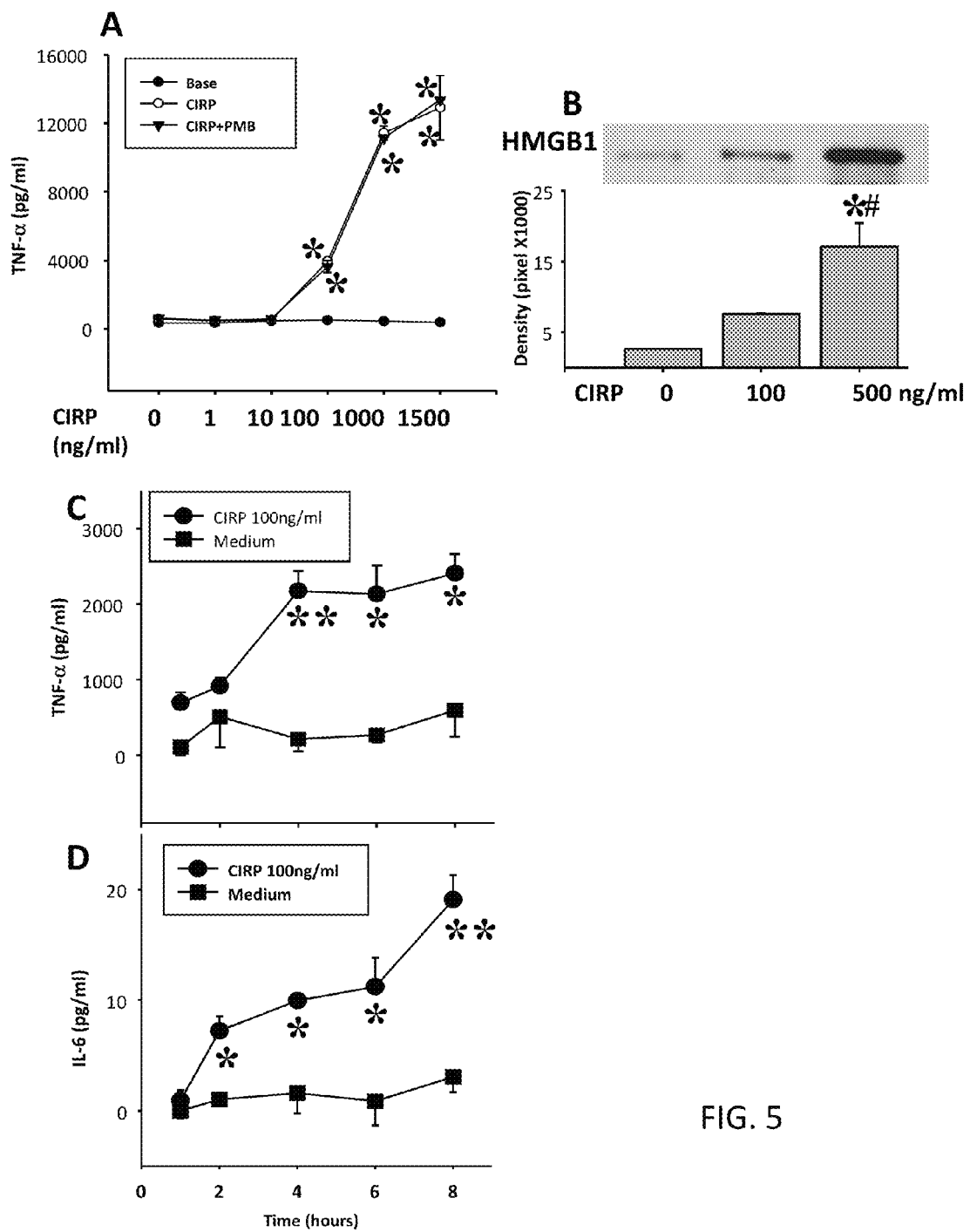
FIG. 5 illustrates the time course and effect of rCIRP to promote and increase cytokine release from cultured macrophages (TNF, IL-6, HMGB1).

Increased Release of Inflammatory Cytokines after Stimulation of Macrophages with rCIRP:

In parallel experiments, we measured cytokines in the supernatant of cultured RAW cells incubated with rCIRP. The elevated TNF-α and IL-6 levels in the supernatants of cultured RAW cell incubated with recombinant CIRP were dose- and time-dependent. As indicated in FIG. 5A, rCIRP at the dose of 100 ng/ml (4-h incubation) significantly increased TNF-α release. With regard to the time course, rCIRP at the dose of 100 ng/ml markedly increased TNF-α and IL-6 production as early as 4 and 2 h after incubation, respectively (FIGS. 5C-D). Supernatant HMGB1 level increased following rCIRP stimulation in a dose-dependent fashion. Quantifying of Western blots showed that HMGB1 release from culture RAW cell increased by ~6 fold after 20 h incubation with rCIRP at the dose of 500 ng/ml (FIG. 5B).

Figure 6:
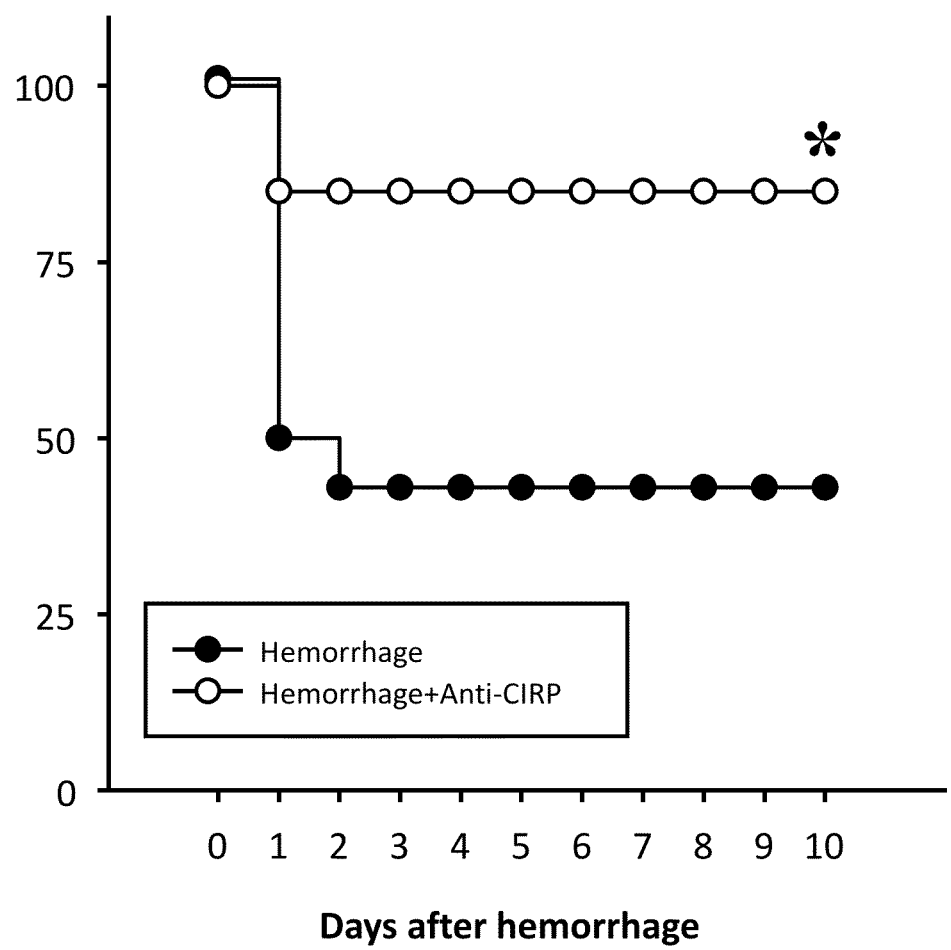
FIG. 6 is a graph illustrating the increase in survival rate by addition of anti-CIRP antibodies in animal models of hemorrhage compared with untreated control.

Anti-CIRP Antibodies Offer Significant Survival Advantage after Hemorrhage:

To further confirm that CIRP is a novel mediator in inflammatory responses to various challenges, such as hemorrhage, we administrated specific antibodies against CIRP (3 mg/kg BW) to hemorrhagic rats. The results showed that that CIRP blockade provides a significant survival advantage in the of acute blood loss. As shown in FIG. 6, anti-CIRP antibody treatment increased the survival rate of experimentally hemorrhaged animals from 43% to 85% ($P<0.05$).

Anti-CIRP Antibodies Attenuate Tissue Injury after Hemorrhage:

To continue to investigate the pathophysiological consequences of rCIRP in the response to hemorrhage, we administrated specific antibodies against CIRP (3 mg/kg BW) to hemorrhagic rats. Our results indicated that the increased levels of AST, ALT, and lactate after hemorrhage was significantly attenuated by anti-CIRP antibodies (decreased by 30~40%, $P<0.05$) (FIGS. 7A-C).

Anti-CIRP Antibodies Attenuate Hemorrhage-Induced Increase in Proinflammatory Cytokines:

Treatment with anti-CIRP antibodies (3 mg/kg BW) significantly decreased hemorrhage-induced upregulation of TNF-α (FIG. 8A) and IL-6 (FIG. 8D) in the serum. Very similar results were also observed in tissue levels of TNF-α (FIGS. 8B and C) and IL-6 (FIGS. 8E and F) in the lungs and liver, respectively, of animals following experimental blood depletion (hemorrhage).

Anti-CIRP Antibodies Reduce the Increased MPO Activity after Hemorrhage:

MPO (myeloperoxidase) is considered a general index of inflammation, and the increased tissue MPO activity reflects neutrophil extravasation. Experimental hemorrhage induced an increase in MPO activity in the liver. We have observed that the increased MPO was significantly reduced after the administration of anti-CIRP antibodies (FIG. 8G).

All references cited in this specification are hereby incorporated by reference.

What is claimed is:

1. A method of treating a subject suffering from an inflammatory condition comprising:
   administering to the subject in need thereof an effective amount of an inhibitor of Cold-Inducible RNA-binding Protein (a CIRP inhibitor);
   wherein the inflammatory condition is ischemia, organ ischemia-reperfusion injury, sepsis, or sepsis-septic shock; and
   wherein the CIRP inhibitor is an antibody or a functional fragment thereof that specifically binds to CIRP; and
   wherein the antibody or functional fragment thereof inhibits one or more biological activities of CIRP.

2. The method of claim 1, wherein the antibody is a polyclonal antibody.

3. The method of claim 1, wherein the antibody is a monoclonal antibody.

4. The method of claim 1, wherein the antibody is a chimeric antibody, human antibody, or humanized antibody.

5. The method of claim 1, wherein the antibody is a single chain antibody.

6. The method of claim 1, wherein the subject is a human.

7. The method of claim 1, wherein the CIRP inhibitor is a monoclonal antibody or a functional fragment thereof that specifically competes for binding to CIRP against rabbit polyclonal antiserum against CIRP raised by injecting rabbits with purified recombinant CIRP of SEQ ID NO: 1.

* * * * *

```
                          SEQUENCE LISTING

<160> NUMBER OF SEQ ID NOS: 11

<210> SEQ ID NO 1
<211> LENGTH: 172
<212> TYPE: PRT
<213> ORGANISM: Homo sapiens

<400> SEQUENCE: 1

Met Ala Ser Asp Glu Gly Lys Leu Phe Val Gly Gly Leu Ser Phe Asp
 1               5                  10                  15

Thr Asn Glu Gln Ser Leu Glu Gln Val Phe Ser Lys Tyr Gly Gln Ile
            20                  25                  30

Ser Glu Val Val Val Lys Asp Arg Glu Thr Gln Arg Ser Arg Gly
        35                  40                  45

Phe Gly Phe Val Thr Phe Glu Asn Ile Asp Ala Lys Asp Ala Met
 50                  55                  60

Met Ala Met Asn Gly Lys Ser Val Asp Gly Arg Gln Ile Arg Val Asp
65                  70                  75                  80

Gln Ala Gly Lys Ser Ser Asp Asn Arg Ser Arg Gly Tyr Arg Gly Gly
                85                  90                  95

Ser Ala Gly Gly Arg Gly Phe Phe Arg Gly Gly Arg Gly Arg Gly Arg
            100                 105                 110

Gly Phe Ser Arg Gly Gly Gly Asp Arg Gly Tyr Gly Gly Asn Arg Phe
        115                 120                 125

Glu Ser Arg Ser Gly Gly Tyr Gly Gly Ser Arg Asp Tyr Tyr Ser Ser
    130                 135                 140

Arg Ser Gln Ser Gly Gly Tyr Ser Asp Arg Ser Ser Gly Gly Ser Tyr
145                 150                 155                 160

Arg Asp Ser Tyr Asp Ser Tyr Ala Thr His Asn Glu
                165                 170

<210> SEQ ID NO 2
<211> LENGTH: 21
<212> TYPE: DNA
<213> ORGANISM: Artificial Sequence
<220> FEATURE:
<223> OTHER INFORMATION: sense primer for rat CIRP coding sequence

<400> SEQUENCE: 2
caccatggca tcagatgaag g                                          21

<210> SEQ ID NO 3
<211> LENGTH: 20
<212> TYPE: DNA
<213> ORGANISM: Artificial Sequence
<220> FEATURE:
<223> OTHER INFORMATION: antisense primer for rat CIRP coding sequence

<400> SEQUENCE: 3
ctcgttgtgt gtagcatagc                                            20

<210> SEQ ID NO 4
<211> LENGTH: 23
<212> TYPE: DNA
<213> ORGANISM: Artificial Sequence
<220> FEATURE:
<223> OTHER INFORMATION: forward primer for measuring rat CIRP
      expression level
```

```
<400> SEQUENCE: 4
gggtcctaca gagacagcta cga                                          23

<210> SEQ ID NO 5
<211> LENGTH: 20
<212> TYPE: DNA
<213> ORGANISM: Artificial Sequence
<220> FEATURE:
<223> OTHER INFORMATION: reverse primer for measuring rat CIRP
      expression level

<400> SEQUENCE: 5
ctggacgcag agggcttttta                                             20

<210> SEQ ID NO 6
<211> LENGTH: 20
<212> TYPE: DNA
<213> ORGANISM: Artificial Sequence
<220> FEATURE:
<223> OTHER INFORMATION: forward primer for measuring rat G3PDH
      expression level

<400> SEQUENCE: 6
atgactctac ccacggcaag                                              20

<210> SEQ ID NO 7
<211> LENGTH: 20
<212> TYPE: DNA
<213> ORGANISM: Artificial Sequence
<220> FEATURE:
<223> OTHER INFORMATION: reverse primer for measuring rat G3PDH
      expression level

<400> SEQUENCE: 7
ctggaagatg gtgatgggtt                                              20

<210> SEQ ID NO 8
<211> LENGTH: 20
<212> TYPE: DNA
<213> ORGANISM: Artificial Sequence
<220> FEATURE:
<223> OTHER INFORMATION: forward primer for measuriing rat TNF-alpha
      expression level

<400> SEQUENCE: 8
cccagaccct cacactcaga                                              20

<210> SEQ ID NO 9
<211> LENGTH: 20
<212> TYPE: DNA
<213> ORGANISM: Artificial Sequence
<220> FEATURE:
<223> OTHER INFORMATION: reverse primer for measuring rat TNF-alpha
      expression level

<400> SEQUENCE: 9
gccactactt cagcatctcg                                              20

<210> SEQ ID NO 10
<211> LENGTH: 26
<212> TYPE: DNA
<213> ORGANISM: Artificial Sequence
<220> FEATURE:
<223> OTHER INFORMATION: forward primer for measuring rat G3PDH
      expression level

<400> SEQUENCE: 10
```

```
tgaaggtcgg tgtcaacgga tttggc                                          26

<210> SEQ ID NO 11
<211> LENGTH: 24
<212> TYPE: DNA
<213> ORGANISM: Artificial Sequence
<220> FEATURE:
<223> OTHER INFORMATION: reverse primer for measuring rat G3PDH
      expression level

<400> SEQUENCE: 11
catgtaggcc atgaggtcca ccac                                            24
```